United States Patent [19]
Arrow et al.

[11] Patent Number: 5,849,902
[45] Date of Patent: Dec. 15, 1998

[54] THREE COMPONENT CHIMERIC ANTISENSE OLIGONUCLEOTIDES

[75] Inventors: Amy Arrow, Newtown, Conn.; Roderic M.K. Dale, Wilsonville, Oreg.; Tod Mitchell Woolf, 21 Birch Rd., Natick, Mass. 01760

[73] Assignees: Oligos Etc. Inc., Wilsonville, Oreg.; Tod Mitchell Woolf, Natick, Mass.

[21] Appl. No.: 754,580

[22] Filed: Nov. 21, 1996

Related U.S. Application Data

[60] Provisional application No. 60/026,732 Sep. 26, 1996.
[51] Int. Cl.$^6$ .............................. C02Q 1/68; C07H 21/04
[52] U.S. Cl. ..................... 36/24.5; 435/91.1; 435/375; 435/6; 536/23.1; 536/24.3; 536/24.5
[58] Field of Search ............................ 435/91.1; 536/375, 536/23.1, 24.5, 24.3; 514/44

[56] References Cited

U.S. PATENT DOCUMENTS

| | | | |
|---|---|---|---|
| 5,576,208 | 11/1996 | Monia et al. | 435/375 |
| 5,582,986 | 12/1996 | Monia et al. | 435/6 |
| 5,652,356 | 7/1997 | Agrawal | 536/24.5 |

OTHER PUBLICATIONS

Gewirtz et al. Science 93;3161–3163 (1996).

Moulds et al. Biochemistry 34:5044–5053 (1995).

De Mesmaeker et al. Current Opinion In Structural Biology 1995, 5:343–355.

*Primary Examiner*—John L. LeGuyader
*Attorney, Agent, or Firm*—Pennie & Edmonds LLP

[57] ABSTRACT

This invention relates to antisense oligonucleotides that target mRNAs in cells as substrates for the cellular enzyme RNase H and thereby cause specific degradation of the targeted mRNA. The oligonucleotides have three components: a RNase H activating region, a complementarity region and 3' and 5' ends. The invention optimizes each of the components to resist intracellular nucleases, to increase hybridization to target mRNA, to specifically inactivate target mRNA in cells, and to decrease cytotoxicity.

23 Claims, No Drawings

SEQUENCE LISTING

<160> 1 (Number of Seq. ID No.s)

<210> 1
<211> 25
<212> DNA
<213> Artificial Sequence

<220>
<223> Description of Artificial Sequence:oligonucleotide

<400> 1
ttgcccacac cgacggcgcc cacca                                                    25

THREE COMPONENT CHIMERIC ANTISENSE OLIGONUCLEOTIDES

The present application claims priority to U.S. Provisional application Ser. No. 60/026,732, filed Sep. 26, 1996 by Tod M. Woolf.

BACKGROUND TO THE INVENTION

Antisense polynucleotides are useful for specifically inhibiting unwanted gene expression in mammalian cells. They can be used to hybridize to and inhibit the function of an RNA, typically a messenger RNA, by activating RNase H.

The use of antisense oligonucleotides has emerged as a powerful new approach for the treatment of certain diseases. The preponderance of the work to date has focused on the use of antisense oligonucleotides as antiviral agents or as anticancer agents (Wickstrom, E., Ed., *Prospects for Antisense Nucleic Acid Therapy of Cancer and AIDS*, New York: Wiley-Liss, 1991; Crooke, S. T. and Lebleu, B., Eds., *Antisense Research and Applications*, Boca Raton: CRC Press, 1993, pp. 154–182; Baserga, R. and Denhardt, D. T., 1992, *Antisense Strategies*, New York: The New York Academy of Sciences, Vol. 660; Murray, J. A. H., Ed., *Antisense RNA and DNA*, New York: Wiley-Liss, 1993).

There have been numerous disclosures of the use of antisense oligonucleotides as antiviral agents. For example, Agrawal et al. report phosphoramidate and phosphorothioate oligonucleotides as antisense inhibitors of HIV. Agrawal et al., *Proc. Natl. Acad. Sci. USA* 85, 7079–7083 (1988). Zamecnik et al. disclose antisense oligonucleotides as inhibitors of Rous sarcoma virus replication in chicken fibroblasts. Zamecnik et al., *Proc. Natl. Acad. Sci. USA* 83, 4143–4146 (1986).

The principal mechanism by which antisense oligonucleotides affect the level of the target RNA is by activation of RNase H, which cleaves the RNA strand of DNA/RNA hybrids. Both phosphodiester and phosphorothioate-linked DNA activates endogenous RNase H, thereby cleaving the targeted RNA (Agrawal, S., et al., *Proc. Natl. Acad. Sci. USA* 87, 1101–5 (1990); Woolf, T. M., et al., *Nucleic Acids Res.* 18, 1763–9 (1990)). However, phosphodiester-linked DNA is rapidly degraded by cellular nucleases and, with the exception of the phosphorothioate-linked DNA, nuclease resistant, non-naturally occurring DNA derivatives do not activate RNase H when hybridized to RNA. While phosphorothioate DNA has the advantage of activating RNase H, phosphorothioate-linked DNA has non-specific cytotoxic effects and also has reduced affinity for RNA (Stein, C. A., et al., *Aids Res Hum Retroviruses* 5, 639–46 (1989); Woolf, T. M., et al., *Nucleic Acids Res.* 18, 1763–9 (1990); Kawasaki, A. M., et al., *J. Med. Chem.* 36, 831–41 (1993)).

Chimeric antisense oligos that have a short stretch of phosphorothioate DNA (3–9 bases) have been used to obtain RNase H-mediated cleavage of the target RNA (Dagle, J. M., et al., *Nucleic Acids Res.* 18, 4751–7 (1990); Agrawal, S., et al., *Proc. Natl. Acad. Sci. USA* 87, 1401–5 (1990); Monia, B. P. et al., 1993, J. Biol. Chem. 268, 14514) A minimum of 3 DNA bases is required for activation of bacterial RNase H (Futdon, P. J., et al., *Nucleic Acids Res.* 17, 9193–9204; Quartin, R. S., et al., *Nucleic Acids Res.* 17, 7235–7262) and a minimum of 5 bases is required for mammalian bacterial RNase H activation (Monia, B. P., et al., *J. Biol. Chem.* 268, 14514–14522 (1993)). In these chimeric oligonucleotides there is a central region that forms a substrate for RNase H that is flanked by hybridizing "arms," comprised of modified nucleotides that do not form substrates for RNase H. Alternatively, extracellular tests using a RNase H-containing HeLa cell extract have been reported wherein the RNase H activating region was placed on the 5' or 3' side of the oligomer. Specifically these tests reported that a 5' or 3' terminal RNase H activating region composed of phosphodiester 2'-deoxynucleotides joined to a methylphosphonate-linked complementarity region was fully active, but that a 5' terminal RNase H-activating region composed of phosphorothioate 2'-deoxynucleotides joined to a methylphosphonate-linked complementarity region was only partially active. See Col 10, U.S. Pat. No. 5,220,007 to T. Pederson et al.

2'-O-Methyl or 2'-fluoro modified nucleotides have been used for the hybridizing arms of chimeric oligos. Inoue, H., et al., 1987, *Nucleic Acids Res.* 15, 6131–48. The 2'-O-Methyl group increases the affinity of the oligomer for the targeted RNA and increases the activity of the oligomer in cell culture. However, 2'-O-Methyl bases with phosphodiester linkages are degraded by exonucleases and so are not suitable for use in cell or therapeutic applications of antisense. Shibahara, S., et al., 1989, *Nucleic Acids Res.* 17, 239–52. Phosphorothioate 2'-O-Methyl nucleotides are resistant to nucleases as shown in the uniformly phosphorothioate modified oligos described by Monia B. P., et al., 1993, *J. Biol. Chem.* 268, 14514–14522 and terminal phosphorothioate substituted, 2'-O-Methylribo-oligonucleotides, Shibahara, S., et al., 1989, *Nucleic Acid Res.* 17, 239–252. However, fully phosphorothioate substituted oligomers may cause non-specific effects including cell toxicity. Stein, C. A., et al., 1989, *Aids Res. Hum. Retrov.* 5, 639–646; Woolf, T. M., et al., 1990, *Nucleic Acids Res.* 18,1763–69; Wagner, R. W., 1995, *Antisense Res. Dev.* 5, 113–115; Krieg, A. M., & Stein, C. A., 1995, *Antisense Res. Dev.* 5, 241. The effects of 2'-Fluoro-oligonucleotides on bacterial RNase H are discussed in Crooke, S. T. et al., 1995, *Bioch. J.* 312, 599–608 and Iwai, S. et al., 1995, *FEBS Lett (Neth.)* 368, 315–20.

Several other chemistries have been used to make the "arms" or regions of a chimeric oligomer that are not substrates for RNase H. The first chimeric oligomers used methylphosphonate or phosphoramidate linkages in the arms (Dagle, J. M., Walder, J. A. & Weeks, K. L., *Nucleic Acids Res.* 18, 1751–7 (1990); Agrawal, S., et al., *Proc. Natl. Acad. Sci. USA* 87, 1401–5 (1990). While these compounds functioned well in buffer systems and Xenopus oocytes, the arms decreased the hybrid affinity. This decrease in affinity dramatically reduces the activity of oligomers in mammalian cell culture.

A number of studies have been reported for the synthesis of ethylated and methylated phosphotriester oligonucleotides and their physico-chemical and biochemical evaluation. Dinucleotides with methyl and ethyl triesters were shown to possess greater affinity towards polynucleotides possessing complementary sequences (Miller, P. S., et al., *J. Am. Chem. Soc.* 93, 6657, (1971)). However, a few years ago, another group reported lack of, or poor binding affinity of heptaethyl ester of oligothymidine with complementary polynucleotides (Pless, R. C., and Ts'O, P. O. P., *Biochemistry* 16, 1239–1250 (1977)). Phosphate methylated (P-methoxy) oligonucleotides were synthesized and found to possess resistance towards endonuclease digestion (Gallo, K. L., et al. *Nucl. Acid Res.* 18, 7405 (1986)). A P-methoxy 18-mer oligonucleotide was shown to have high Tm value in duplexes with natural DNA and blocked to the DNA replication process at room temperature (Moody, H. M., et al., *Nucl. Acid Res.* 17, 4769–4782 (1989)). Moody et al. stated that phosphate ethylated (P-methoxy) oligonucleotides would have poor antisense properties. P-methoxy dimers of DNA bases were synthesized using transient protecting group of FMOC for the exocyclic amino groups (Koole, L. H., et al., *J. Org. Chem.* 54, 1657–1664 (1989)).

Synthesis and physico-chemical properties of partial P-methoxy oligodeoxyribonucleotides were determined. Only the thymidine and cytidine oligomers with methyl phosphotriester could be prepared satisfactorily due to difficulty in maintaining methyl triester intact. Furthermore, the methyl group was found to have destabilizing effect on the hybridization properties of the modified oligomers with its complementary sequence by comparison with unmodified parent oligodeoxynucleotide (Vinogradeov, S., Asseline, U., Thoung, N. T., *Tet. Let.* 34, 5899–5902 (1993)).

Other reports have suggested that P-methoxy oligonucleotides are preferable to P-ethoxy as antisense olgionucleotides because of p-methoxy oligonucleotides showed stronger hybridization than methyl phosphonate or P-ethoxy oligonucleotides (van Genderen, M. H. P., et al., *Kon. Ned. Akad. van Wetensch.* B90, 155–159 (1987); van Genderen, M. H. P., et al., *Trav. Chim. Pays Bas* 108, 28–35 (1989)). P-ethoxy oligonucleotides were reported by van Genderen et al. to hybridize poorly to DNA, for which reason they were regarded unfavorably as antisense oligonucleotides (Moody, H. M., et al., *Nucl. Acid Res.* 17, 4769–4782 (1989)).

P-isopropoxyphosphoramidites have been synthesized from several nucleosides (Stec, W. J., et al., *Tet. Let.* 26, 2191–2194 (1985)), and a few short oligonucleotides containing P-isopropoxy phosphotriesters were synthesized, and hybridization studies were carried out.

U.S. Pat. No. 5,525,719 to Srivastava, S., and Raza, S. K., Jun. 11, 1996, suggests antisense oligonucleotides consisting of 2'-O-Methyl nucleotides linked by phosphodiester and/or P-ethoxy or P-methoxy, phosphotriester moieties.

Thus, currently there are no nucleic acid chemistries nor any chimeras that have been developed that optimally achieve all the features that are needed to provide an effective antisense oligonucleotide i.e. low toxicity, high specificity, nuclease resistance, ease of synthesis, RNase H compatibility.

SUMMARY OF THE INVENTION

The invention provides a class of oligonucleotide that is optimized to target a specific RNA for RNase H degradation and to be itself resistant to degradation within in plasma and within eukaryotic, especially mammalian cells. The oligonucleotides of the invention contain no naturally occurring 5'→3'-linked nucleotides. Rather, the invention provides oligonucleotides having two types of nucleotides: 2'-deoxyphosphorothioate, which activate RNase H, and 2'-modified nucleotides, which do not. The linkages between the 2'-modified nucleotides can be phosphodiesters, phosphorothioate or P-ethoxyphosphodiester. Activation of RNase H is accomplished by a contiguous, RNase H-activating region, which contains between three and five 2'-deoxyphosphorothioate nucleotides to activate bacterial RNase H and between five and ten 2'-deoxyphosphorothioate nucleotides to activate eukaryotic and, particularly, mammalian RNase H. Protection from degradation is accomplished by making the 5' and 3' terminal bases highly nuclease resistant and, optionally, by placing a 3' terminal blocking group.

In a preferred embodiment the RNase H activating region, which is composed of highly nuclease resistant phosphorothioate nucleotides is placed at the 5' end of the oligonucleotide.

DETAILED DESCRIPTION OF THE INVENTION

The Structure of the Oligonucleotides

An oligonucleotide of the invention is comprised of a 3'-terminal 5'→'-linked nucleoside and from 11 to 59 5'→3' linked nucleotides, which nucleotides can be 2'-deoxynucleotides or 2'-modified nucleotides, modified to enhance the hybridization of the oligonucleotide to the target mRNA, such as 2'-fluoro, 2'-methoxy, 2'-ethoxy, 2'-methoxyethoxy, 2'allyloxy (—OCH$_2$CH=CH$_2$) nucleotides (hereinafter "2'-modified nucleotides"). The 3' terminal nucleoside can, optionally, be 2'-modified nucleoside. Those skilled in the art appreciate that the 3'-OH of the 3' terminal base can but need not be esterified to a phosphate or phosphate analog. The 3' terminal residue is referred to as a nucleoside even though it may be a nucleotide.

The internucleotide linkages of an oligonucleotide of the invention can be phosphodiester, phosphorothioate or P-ethoxyphosphodiester moieties. The oligonucleotide has a 3' terminus and a 5' terminus that are protected from nuclease attack. The 3' terminus is protected by having the 3' most 5'→3' linkage or linkages be a phosphorothioate or a P-alkyloxyphosphotriester linkage and/or by having a substituted 3' terminal hydroxyl, e.g., a 3'→3' linked nucleotide, wherein the alkyloxy radical is methoxy, ethoxy or isopropoxy and, preferably, ethoxy. Preferably two or three 3' terminal internucleotide linkages are phosphorothioate or a P-alkyloxyphosphotriester linkages. To reduce nuclease degradation, the 5' most 3'→5' linkage preferrably should be a phosphorothioate linkage or P-alkyloxyphosphotriester linkage. Preferrably, the two 5' most 3'→5' linkages should be phosphorothioate linkages or P-ethoxyphosphotriester linkages. Optionally, the 5'-terminal hydroxyl moiety can be esterified with a phosphorus containing moiety, e.g., phosphate, phosphorothioate or P-ethoxyphosphate, without limitation.

The 3' terminal 5'→3'-linked nucleoside has a 3'-O that can be optionally substituted by a blocking moiety that prevents 3'-exonuclease degradation of the oligonucleotide. In one embodiment, the 3'-hydroxyl is esterified to a nucleotide through a 3'→3' internucleotide linkage. Optionally, the 3'→3' linked nucleotide at the 3' terminus can be linked by a phosphorothioate moiety.

In a preferred embodiment, the oligonucleotide contains, exclusive of an optional blocking nucleotide, between 15 and 50 bases and more preferably between 20 and 30 bases and in a most preferred embodiment the oligonucleotide is 25 bases in length. The oligonucleotide of the invention contains a single contiguous RNase H-activating region of between three to ten 2'-deoxyphosphorothioate nucleotides. The length of the RNase H activating region to activate bacterial RNase H is preferably between three and five nucleotides; to activate a eukaryotic RNase H it is between five and ten nucleotides. The preferred length of the RNase H-activating region for the activation of mammalian RNase H is nine nucleotides.

All 5'→3' linked nucleotides of the oligonucleotide that are not a part of the RNase H-activating region are 2'-modified nucleotides, which contribute to the target binding and form the complementarity determining region. The complementarity region can be a contiguous region or can be divided by the RNase H-activating region. In the preferred embodiment the complementarity region is a contiguous region, and more preferably is 3' to the RNase H-activating region.

In a preferred embodiment all bases except the from one to three 3' most nucleotides and nucleoside, the 5' terminal nucleotide and RNase H activating region nucleotides are phosphodiester linked. Large amounts of contiguous phosphorothioate linkages are detrimental to the function of the oligonucleotides of the invention. Preferably, therefore, the oligonucleotides contain not more than ten contiguous phosphorothioate linkages.

The Synthesis of the Oligonucleotides

The oligonucleotides of the invention can be synthesized by solid phase or liquid phase nucleotide synthesis, however, synthesis by solid phase techniques is preferred. Phosphodiester and phosphorothioate linked oligonucleotides can be synthesized, using standard reagents and protocols, on an automated synthesizer utilizing methods that are well known in the art, such as, for example, those disclosed in Stec et al., *J. Am. Chem. Soc.* 106, 6077–6089 (1984); Stec et al., *J. Org. Chem.* 50(20), 3908–3913 (1985); Stec et al., *J. Chromatog.* 326, 263–280 (1985); LaPlanche et al., *Nuc. Acid. Res.* 14, 9081–9093 (1986); and Fasman, G. D., *Practical Handbook of Biochemistry and Molecular Biology* 1989, CRC Press, Boca Raton, Fla., herein incorporated by reference.

The synthesis of 2'-O-alkyl-oligoribonucleotides, where the alkyl groups are methyl, butyl, allyl or 3,3-dimethylallyl is reviewed by Lamond, *Biochem. Soc. Trans.* 21, 1–8 (1993). Intermediates that are useful in the synthesis of 2'-O-methyl oligoribonucleotides are described in U.S. Pat. No. 5,013,830, No. 5,525,719 and No. 5,214,135, which are hereby incorporated by reference.

The synthesis of 2'-fluorophosphodiester and 2'-fluorophosphorothioate oligonucleotides can be performed according to teaching of Kawasaki, A. M., et al., 1993, *J. Med. Chem.* 36, 831–41 and WO 92/03568; the synthesis of P-alkyloxyphosphotriester-linked oligonucleotides and 2'-modified oligonucleotides can be performed according to U.S. Pat. No. 5,525,719, each of which is incorporated herein by reference. The synthesis of phosphorothioate oligodeoxynucleotides is taught by U.S. Pat. No. 5,276,019 and No. 5,264,423, which is hereby incorporated by reference. Synthesis of 2'-substituted oligonucleotides can be performed by variations on the techniques disclosed therein.

The synthesis of the oligonucleotides of the invention must be conducted with great attention to quality control. It is particularly important that the phosphorothioate linkages not be contaminated with phosphodiester linkages. It is advisable to pre-test the individual reagent lots to ascertain that high coupling efficiency can be obtained therewith and to exercise all possible precautions to maintain anhydrous conditions.

The quality of the synthesis of oligonucleotides can be verified by testing the oligonucleotides by capillary electrophoresis and denaturing strong anion HPLC (SAX-HPLC). The method of Bergot & Egan, 1992, *J. Chrom.* 599, 35–42 is suitable. SAX-HPLC is particularly useful to verify that the phosphorothioate nucleotides are completely thiolated, i.e., are not contaminated by a small percentage of phosphodiesters.

The synthesis of oligonucleotides having both phosphodiester and phosphorothioate linkages is associated with a side reaction whereby the phosphorothioate linkages are oxidized by the standard $I_2$ treatments that are used to oxidize the cyanoethyl phosphoramidite. This problem can be minimized but not eliminated by reducing the concentration or $I_2$ to as low as 0.001M. Therefore, in a preferred embodiment, all phosphorothioates of the oligonucleotides of the invention are found at the 5'-end, so that no phosphorothioate bond is exposed to $I^2$.

The Uses of the Oligonucleotides

The oligonucleotides of the invention can be used as antisense oligonucleotides in a variety of in vitro experimental situations to specifically degrade an mRNA of unknown function and thereby determine its physiologic function.

The oligonucleotides of the invention can be also used in clinical practice for any disease and against any target RNA for which antisense therapy is now known to be suitable or which is yet to be identified. Medical conditions for which antisense therapy is reported to be suitable includes Respiratory Syncytial Virus infection, WO 95/22553 by Kilkuskie, Influenza Virus infection, WO 94/23028, and malignancies, WO 94/08003. Further examples of clinical uses of antisense oligonucleotides are reviewed, in summary form, in Glaser, V., 1996, *Genetic Engineering News* 16, 1. Targets of antisense oligonucleotides under that are the subjects of clinical trials include protein kinase Cα, ICAM-1, c-raf kinase, p53, c-myb and the bcr/abl fusion gene found in chronic myelogenous leukemia.

EXAMPLES

Experimental Conditions

The oligonucleotides of the invention are demonstrated by a test transient expression system which includes an mRNA encoding the luciferase protein that has been modified to include a test sequence derived from the ras gene. The specific antisense effects of an oligonucleotide can be measured by comparing the luciferase production of the test cells with the production of control cells having the same expression plasmid except for the absence of the ras-derived sequence. The oligonucleotides of the invention tested have the sequence:

5'-TTGCCCACACCGACGGCGCCCACCA-3' (SEQ ID NO: 1)

The details of the assay are as follows:

Plasmid Constructs. The plasmid used for the studies contained a portion of the ras gene sequence fused to luciferase (Monia, B. P., et al. *J. Biol. Chem.* 267, 19954–19962 (1992)). The control luciferase plasmids did not contain the ras target sequence.

Cell Culture Assay. HeLa cells were grown to 40–90% confluence in DMEM/10% FBS, Supplemented with glutamine, penicillin and streptomycin on gelatin coated 24 well plates. The gelatin coating was necessary for cell to remain adherent during the transfections. Prior to transfection the cells were washed twice with PBS (containing magnesium and calcium). LIPOFECTIN™ was mixed gently and 6.6 μl was added for each milliliter of reduced serum medium (OPTI-MEM™, Gibco/BRL, Gaithersberg, Md.). Oligomers were added from 50–100 μM concentrated stock to make a master mixture. The Opti-MEM/LIPOFECTIN/oligomer solution was added to the cells and incubated for 4 hours (≈0.5 mls for one well of a 24 well plate).

A target transfection mixture was prepared by first diluting 5 μl of lipofectin per ml of OPTI-MEM and mixing. Next 5 μg of luciferase target and 5 μg of CMV β-galactosidase were added per milliliter of OPTI-MEM/LIPOFECTINT™ mixture. The transfection mixture was mixed gently and allowed to complex for about 15 minutes. The master mixture reduced error by assuring that the control and experimental cells received the exact same cationic lipid/plasmid complex. The concentration of oligonucleotide in the culture medium was between 200 nM and 400 nM in all experiments. The oligonucleotide containing media was removed from the cells and replaced with growth media and incubated for an additional 9–18 hours. The cell were rinsed with calcium and magnesium free media and the media was removed. The plates were frozen at −70 for >20 minutes and 100–300 μl of reporter lysis buffer (Promega, Madison Wis.) was added.

The cells were put through 2 more freeze thaw cycles, to assure complete lysis. Luciferase assays were preformed according to the manufacture's instructions (Promega, Madison Wis.) and luminescence was detected with a 96 well luminometer (Packard, Meriden Conn.). β-galactosidase assays were preformed (Galacton Plus, Tropix) according to manufactures instructions and detected on the Packard luminometer.

Experimental Results

The results of luciferase assay are presented in Table I below. The results are reported as the percent specific inhibition which were calculated as $100 \times (1 - (LUC_T/LUC_C)^{OLIGO}/(LUC_T/LUC_C)^{NO\ OLIGO})$; wherein $LUC_T$ and $LUC_C$ are the luciferase levels found in the cells transfected with luciferase plasmids containing and lacking the ras gene insert (SEQ ID NO: 1); and the superscripts "Oligo" and "No Oligo" refer to the presence and absence of antisense oligonucleotides.

TABLE I

| Oligo | Formula | Specific inhibition |
|---|---|---|
| | Controls ("C") | |
| C1 | 25Mo | 26% |
| C2 | 25Ms | 15% |
| C3 | 9Ds16Mo | 15% |
| C4 | 9Do16MoInVT | 0% |
| C5 | 9Dp16MoInVT | 18% |
| C6 | 9Dp13Mo3Ms | 14% |
| | Controls with all "S" | |
| S1 | 25Ds | 93% |
| S2 | 16Ms8DsD | 100% |
| S3 | 8Ms9Ds7MsM | 97% |
| S4 | 9Ds15MsM | 95% |
| | 9Ds at 3' end ("3'I") | |
| 3'I1 | InvTMs15Mo9DsInvT | 59% |
| 3'I2 | 2Ms14Mo9DsInvT | 57% |
| 3'I3 | 4Ms12Mo9DsInvT | 65% |
| | 9Ds in Middle ("MI") | |
| MI1 | 5Ms3Mo9Ds4Mo3MsM | 64% |
| MI2 | 2Ms6Mo9Ds7 (MsMo) InvT | 71% |
| MI3 | 3Ms6Mo9Ds6MoMsInvT | 87% |
| | 9Ds at 5' end ("5'I") | |
| 5'I1 | 9Ds16MoInvT | 83% |
| 5'I2 | 9Ds15MoMsInvT | 85% |
| 5'I3 | 9Ds16MoBiotin | 90% |
| 5'I4 | 9Ds16Mp | 91% |
| 5'I5 | 9Ds14MoMpD | 90% |
| 5'I6 | 9Ds13Mo2MpD | 94% |
| 5'I7 | 9Ds12Mo3MpD | 94% |
| 5'I8 | 9Ds14MoMsD | 93% |
| 5'I9 | 9Ds13Mo2MsD | 97% |
| 5'I10 | 9Ds12Mo3MsD | 95% |

Key: M and D refer to 2'O-methyl- and 2'deoxy-ribonucleotides, respectively. The letters "o", "s" and "p" refer to phosphodiester, phosphorothioate diester, and P-ethoxy-phosphotriester linked nucleotides. "InvT" referes to a 3'→3' or 5'→5' linked thymidine at the 3' or 5' end, respectively.

Table I shows the results of control oligos C1–C6, all phosphorothioate oligos S1–S4, and oligos of the invention having the RNase activating region at the 3' end (3'I1–3'I3), in the middle (MI1–MI3) and at the 5' end (5'I1–5'I10). Control oligos C1, C2, C5 and C6 showed low levels of specific inhibition because these oligos lacked an RNase H activating region. Oligos C3 and C4 were inactive because the 3' was unprotected and because native ssDNA was unstable, respectively. All phosphorothioate oligonucleotides (S1–S4) showed specific inhibitions that ranged between 93% and 100%, as did oligonucleotides 5'I6–5'I10, which have a 5'-located RNase H activating region and two or three 3' terminal 2'O-methyl modified P-ethoxy or phosphorothioate linked nucleotides (Mp and Ms, respectively). Lower levels of specific inhibition were observed when oligonucleotides with 3' and mid-located RNase H activating regions were employed or when suboptimal 3' protecting groups were present.

Although the oligonucleotides of the invention having 5' RNase activating regions achieved specific inhibitions which were comparable to that achieved by the uniform phosphorothioate oligonucleotides, the oligonucleotides of the invention were superior in that their use was associated with significantly less toxicity. Table II shows specific inhibition, the average metabolic activity as percent of no oligo control, as determined by MTS assay, and the percent viable cells, as determined by trypan blue exclusion for the conventional ("C"), all phosphorothioate ("S"), 3'I, MI and 5'I oligonucleotides, as well as for three species.

TABLE II

| Oligo | % INH Luc | % of Control Metabolic Activity | % of Viable Cells |
|---|---|---|---|
| All "O" Oligos C1–C6 | 15% | 94% | 76% |
| All "S" Oligos S1–S4 | 96% | 25% | 21% |
| 3'I (1–4) | 60% | 70% | 61% |
| MI (1–3) | 74% | 77% | 67% |
| 5'I (1–10) | 91% | 71% | 60% |

The best oligos on the chart have high percentage values in all columns.

The results demonstrated that the oligonucleotides of the invention achieve levels of specific inhibition more than four times greater than conventional oligonucleotides while showing toxicity levels that were substantially less than the phosphorothioate oligonucleotides. The optimal group, 5'I, showed specific inhibition that was comparable to the phosphorothioate oligonucleotides.

The Effect of the Location of the RNase H ACTIVATING REGION

The cause of lower specific activity observed for the 3'I and MI type oligonucleotides was investigated. One possibility was that the oxidation steps using 0.02M I$_2$ cause the oxidation of the phosphorothioate linkages to phosphodiester, when phosphodiester linked nucleotides were added 5' to the phosphorothioate linkages. This was found to be the case. Comparison of oligonucleotides $9D_S15D_OD$ ("5'S") and $15D_O9D_SD$ ("3'S") oligonucleotides having the sequence of the test oligonucleotide by analytical HPLC analysis showed that about 85% of the 5'S oligonucleotides were fully thiolated, by contrast only 26% of the 3'S oligonucleotides were completely thiolated (36% were S-1, 24% S-2 and 14% S-3).

Table III shows the distribution of fully thiolated and mono, di and tri-oxidized by-products as a function of the position of the phosphorothiolated region of the oligonucleotide. Four thymidyl pentadodecamers were synthesized using 0.02M I$_2$ as the oxidant for 15 nucleotides and a thiolating agent for nine nucleotides.

TABLE III

| Ts | [I₂] | S | S-1 | S-2 | S-3 |
|---|---|---|---|---|---|
| 5'-9Ds15DoD03' | 0.02M | 96% | 4% | — | — |
| 5'-1Do9Ds14DoD-3' | 0.02M | 85% | 15% | — | — |
| 5'-8Do9Ds7DoD-3' | 0.02M | 41% | 46% | 12.5 | 0.5 |
| 5'-15Do9DSD-3' | 0.02M | 32% | 43% | 20% | 5% |
| 5'-15Do9DsD-3' | 0.001M | 78% | 14% | 8% | — |

The results demonstrated that 96% of the 5'S oligonucleotides are fully thiolated, which percentage steadily decreases as the phosphorothioate region is exposed to more frequent oxidation reactions. When the oxidant concentration was reduced to 0.001M, 78% fully thiolated 3'S 25-T oligonucleotides and about 60% of oligonucleotides having the sequence of the SEQ ID NO: 1 were synthesized.

We claim:

1. A chimeric antisense oligonucleotide comprising: a 5' terminus; a 3' terminus; and from 11 to 59 5'→3'-linked nucleotides independently selected from the group consisting of 2'-modified phosphodiester nucleotides, and 2'-modified P-alkyloxyphosphotriester nucleotides; and wherein said 5' terminal nucleoside is attached to an RNase H-activating region of between three and ten contiguous phosphorothioate-linked deoxyribonucleotides, and wherein the 3' terminus of said oligonucleotide is drawn from the group consisting of: an inverted deoxyribonucleotide, a contiguous stretch of one to three phosphorothioate 2'-modified ribonucleotides, a biotin group, and a P-alkyloxyphosphotriester nucleotide.

2. The oligonucleotide of claim 1, provided the 3' terminus is not blocked by a 3'→3' phosphorothioate linked nucleotide.

3. The oligonucleotide of claim 1, in which the 3' terminus is blocked by a moiety comprising a 3'→3' phosphorothioate linked nucleotide.

4. The oligonucleotide of claim 1, in which the 3' terminus is blocked by a moiety comprising a 3'→3' phosphodiester linked nucleotide.

5. The oligonucleotide of claim 4, in which the 3' most 5'→3' internucleotide linkage is a phosphorothioate linkage or a P-ethoxyphosphotriester linkage.

6. The oligonucleotide of claim 4, in which the 5' most 5'→3' internucleotide linkage is a phosphorothioate linkage or a P-ethoxyphosphotriester linkage.

7. The oligonucleotide of claim 1, in which the 3' terminal nucleoside and the 5' most nucleotide are 2'-modified nucleotides.

8. The oligonucleotide of claim 1, in which the RNase H activating region comprises the 5' most nucleotide.

9. The oligonucleotide of claim 8, in which the 3' most 5'→3' internucleotide linkage is a phosphorothioate linkage or a P-ethoxyphosphotriester linkage.

10. The oligonucleotide of claim 9, in which the two 3' most 5'→3' internucleotide linkages are independently either a phosphorothioate linkage or a P-ethoxyphosphotriester linkage.

11. The oligonucleotide of claim 9, in which all phosphorothioate linkages are contiguous with the 5' most 5'→3' internucleotide linkage.

12. The oligonucleotide of claim 11, in which the 2'-modified nucleotide is a 2'-methoxy or 2'-fluoro nucleotide.

13. The oligonucleotide of claim 11, which comprises at least thirteen 2'-methoxy phosphodiester nucleotides.

14. The oligonucleotide of claim 11, having between 15 and 50 nucleotides.

15. The oligonucleotide of claim 14, which comprises at least eight 2'-methoxy phosphodiester nucleotides.

16. The oligonucleotide of claim 14, which comprises at least thirteen 2'-methoxy phosphodiester nucleotides.

17. A chimeric antisense oligonucleotide, comprising: a 5' terminus; a 3' terminus; and from 11 to 59 5'→3'-linked nucleotides independently selected from the group consisting of 2'-modified phosphodiester nucleotides, and 2'-modified P-alkyloxyphosphotriester nucleotides; and wherein said 3' terminal nucleoside is attached to an RNase H-activating region of between three and ten contiguous phosphorothioate-linked deoxyribonucleotides, and wherein the 5' terminus of said oligonucleotide is drawn from the group consisting of: an inverted deoxyribonucleotide, a contiguous stretch of one to three phosphorothioate 2'-modified ribonucleotides, a biotin group, and a P-alkyloxyphosphodiester nucleotide.

18. The oligonucleotide of claim 1, in which the 2'-modified nucleotides are selected from the group consisting of 2'-fluoro and 2'-methoxy nucleotides.

19. The oligonucleotide of claim 1, in which there are no 2'-modified phosphodiester nucleotides.

20. A method of specifically cleaving an RNA in a cell containing RNase H which comprises administering an effective amount of an oligonucleotide complementary to the RNA comprising: a 5' terminus; a 3' terminus; and from 11 to 59 5'→3'-linked nucleotides independently selected from the group consisting of 2'-modified phosphodiester nucleotides, 2'-modified P-alkyloxyphosphotriester nucleotides; and wherein said 5' terminal nucleoside is attached to an RNase H-activating region of between three and ten contiguous phosphorothioate-linked deoxyribonucleotides, and wherein the 3' terminus of said oligonucleotide is drawn from the group consisting of: an inverted deoxyribonucleotide, a contiguous stretch of one to three phosphorothioate deoxyribonucleotides, phosphorothioate 2'-modified ribonucleotides, a biotin group, and a P-alkyloxyphosphodiester-linked nucleotide.

21. A chimeric antisense oligonucleotide comprising:
   a) a 5' terminal RNase H activation region having between 5 and 10 contiguous deoxyphosphorothioate nucleotides;
   b) between 11 to 59 contiguous 5'→3'-linked 2'-methoxy ribonucleotides; and
   c) an exonuclease blocking group present at the 3' end of the oligonucleotide that is drawn from the group consisting of: a non-5'-3' phosphodiester-linked nucleotide, from one to three contiguous 5'-3'-linked modified nucleotides, and a non-nucleotide chemical blocking group.

22. The oligonucleotide of claim 21, wherein said non-5'-3' phosphodiester-linked nucleotide is drawn from the group consisting of: a 3'—3'-linked nucleotide, a phosphorothioate 2'-modified ribonucleotide, and a P-alkyloxyphosphodiester-linked nucleotide.

23. The oligonucleotide of claim 21, wherein said chemical non-nucleotide chemical blocking group is biotin.

* * * * *